United States Patent [19]

Lam

[11] 4,365,341
[45] Dec. 21, 1982

[54] ON-LINE TREATMENT MONITORING FOR RADIATION TELETHERAPY

[75] Inventor: Wing-Chee Lam, Columbia, Md.

[73] Assignee: The Johns Hopkins University, Baltimore, Md.

[21] Appl. No.: 157,843

[22] Filed: Jun. 9, 1980

[51] Int. Cl.³ .............................................. A61N 5/00
[52] U.S. Cl. ..................................... 378/65; 378/69; 378/99; 378/205
[58] Field of Search ............ 250/491, 492 R, 416 TV, 250/369, 370; 364/414

[56] References Cited

U.S. PATENT DOCUMENTS

| | | | |
|---|---|---|---|
| 3,777,124 | 12/1973 | Pavkovich | 250/454 |
| 3,934,142 | 1/1976 | Hounsfield | 250/360 |
| 3,949,210 | 4/1976 | Eichinger et al. | 250/370 |
| 3,973,128 | 8/1976 | LeMay | 250/445 T |
| 4,002,917 | 1/1977 | Mayo | 250/445 T |
| 4,118,631 | 10/1978 | Froggatt | 250/492 R |
| 4,174,481 | 11/1981 | Liebetruth | 250/491 |
| 4,247,780 | 1/1981 | Webber et al. | 250/491 |
| 4,250,385 | 2/1981 | Luderer et al. | 250/370 |
| 4,262,199 | 4/1981 | Bridges et al. | 250/348 |

FOREIGN PATENT DOCUMENTS

| | | | |
|---|---|---|---|
| 343494 | 8/1973 | U.S.S.R. | 250/491 |
| 519887 | 4/1975 | U.S.S.R. | 250/492 R |

Primary Examiner—Alfred E. Smith
Assistant Examiner—Carolyn E. Fields
Attorney, Agent, or Firm—Cushman, Darby & Cushman

[57] ABSTRACT

A method and apparatus are provided for the on-line treatment monitoring of patients during radiation teletherapy. A patient is positioned in the irradiation portal of the radiation teletherapy machine in a supposed effective treatment position, and operation of the machine is effected to provide several pulses of high energy x-rays. The pulses are detected by a plurality of solid-state detectors disposed on the opposite side of the patient as the teletherapy machine, and the pulses are transformed to electrical signals. Lead covers the detectors to screen out low energy radiation. The electrical signals are immediately automatically converted to a readable display providing the landmarks of the irradiation portal, and the patient's position as defined by the landmarks is compared to a predetermined desired position for effective treatment. In case of misalignment, treatment is halted, the patient's position is then immediately adjusted with respect to the irradiation portal so that it is proper for effective treatment, and the radiation teletherapy machine is then actuated to deliver the desired dosage of radiation to the patient for therapy. The digital data of the image can be stored on magnetic disk or tape for later review.

25 Claims, 6 Drawing Figures

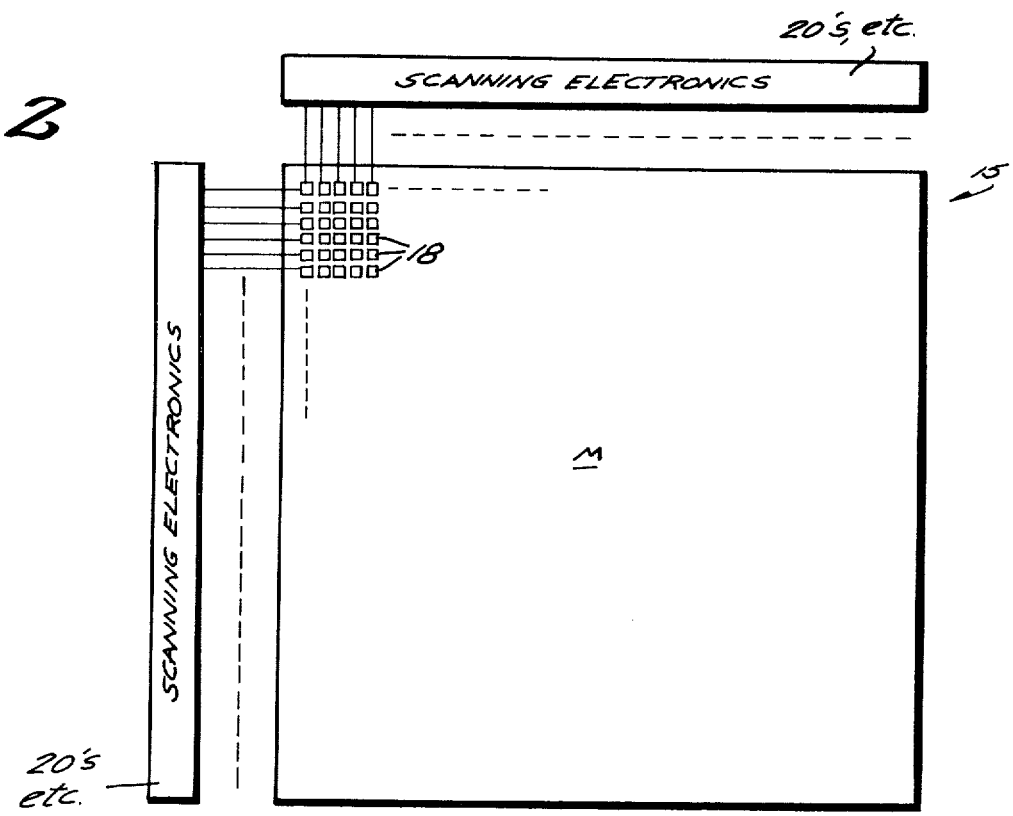
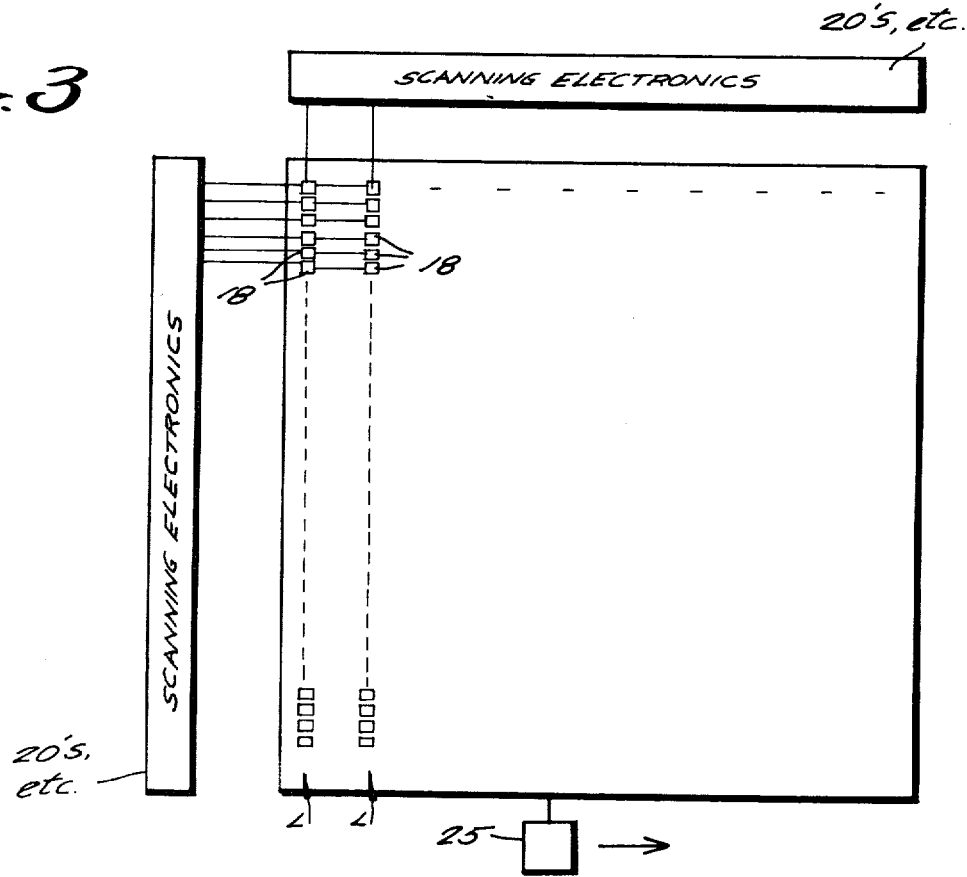

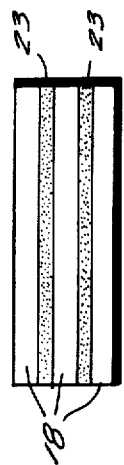
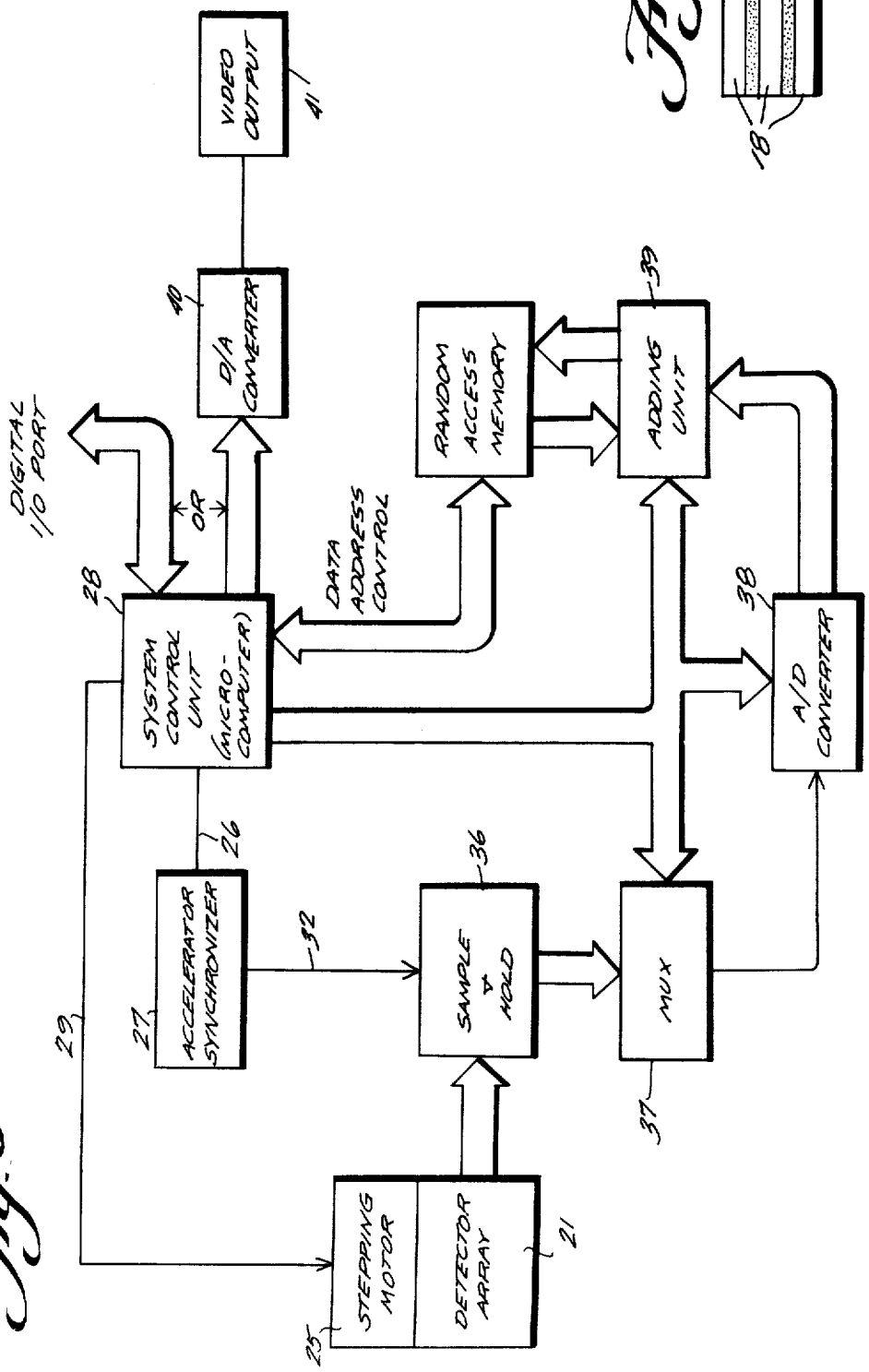

ON-LINE TREATMENT MONITORING FOR RADIATION TELETHERAPY

BACKGROUND AND SUMMARY OF THE INVENTION

In the treatment of patients with high energy x-ray teletherapy machines, there has been a longstanding problem of accurately positioning the patient in the irradiation portal of the teletherapy machine so as to provide maximum effective treatment of the patient's body portions to be treated, while minimizing radiation exposure to other portions. Utilizing present techniques, localization errors are frequent, on the order of about 30%. In addition, present monitoring techniques are slow, and expensive, and are not practiced on-line (that is during actual treatment) so that no direct feedback is provided.

Conventionally, the proper positioning of a patient in the irradiation portal of a radiation teletherapy machine is accomplished during a weekly session specifically for filming the patient for proper positioning, no therapy being practiced during such sessions. The patient is positioned on the treatment couch, between the x-ray source and a film cassette and then the teletherapy machine is actuated for a short period of time. The film cassette is processed and then is reviewed prior to the next therapy session.

According to the present invention, most of the limitations associated with prior art monitoring procedures for radiation teletherapy are overcome, and the long-standing problem in the art with respect to such monitoring is solved. According to the present invention it is possible to accurately position the patient during each treatment session so that the tumor bearing sites will receive precisely the prescribed radiation dosage, while surrounding areas will receive a minimum of radiation. Weekly filming sessions are eliminated as are the needs for film storage and processing space. Additionally, according to the present invention the images produced are much clearer than the images produced during filming sessions, further contributing to the accuracy of patient positioning.

According to the present invention on-line monitoring of the patient position is possible despite the fact that high-energy x-rays are being utilized for therapy as well as to practice the monitoring. The patient's position can be immediately readjusted during a therapy session with instant feedback to the therapy technician to provide accurate information for proper positioning.

According to the present invention there is provided a method for treating a patient with radiation therapy utilizing a radiation teletherapy machine having high-energy x-rays. In practicing the method, the patient is positioned in the irradiation portal of the radiation teletherapy machine in a supposed effective treatment position. Operation of the machine is then effected to provide pulses of high-energy x-rays for treatment. The several pulses of x-rays are automatically detected and transformed to electrical signals, preferably by utilizing a plurality of solid-state detectors covered by filtering means preventing the passage of low energy scattered radiation to the detectors, and positioned on the opposite side of the patient as to the radiation source. The electrical signals are immediately automatically converted to a readable display providing the landmarks of the irradiation portal. Then the patient's position as defined by the landmarks is compared to the predetermined desired position for effective treatment of the tumor, and if necessary the patient's position is immediately adjusted with respect to the irradiation portal so that it is proper for effective treatment. The provision of a readable display for a patient position may be repeated, with subsequent adjustment of the patient's position, until the exact position is obtained. Once the patient is in proper position the radiation therapy is continued to deliver the desired dosage of radiation to the patient.

According to the present invention there is also provided apparatus for on-line treatment monitoring for radiation teletherapy. The apparatus comprises a radiation teletherapy machine for emitting high-energy x-ray pulses in an irradiation portal, a patient treating couch, and detecting means for detecting high-energy x-rays emitted from the radiation teletherapy machine and transmitted through the patient, and transforming the x-rays detected into electrical signals. The detecting means are located on the opposite side of the patient treatment couch as the radiation teletherapy machine. The apparatus further comprises filtering means covering the detecting means for preventing low energy scattered radiation from reaching the detecting means, and means for converting the electrical signals produced by the detecting means to a readable display providing patient landmarks of the irradiation portal. Preferably the detecting means comprise a plurality of solid-state photon detectors, such as silicon, cadmium telluride, or mercuric iodide detectors. The detectors may be disposed in a two-dimensional matrix covering the irradiation portal, or one or more linear arrays of detectors may be provided. Where linear arrays are provided a stepping motor is utilized to move the array over at least a portion of the irradiation portal in sync with the emission of x-ray pulses from the radiation teletherapy machine.

The means for converting the electrical signals produced by the detecting means to a readable display preferably include the following: An amplifier associated with each detector. A sample and hold means associated with each detector. Means for connecting the sample and hold means to the radiation machine through a proper timing delay for controlling the sample and hold means. A multiplexer connected to the output of the sample and hold means. An analog/digital converter means operatively attached to the output of the multiplexer. Adding means operatively attached to the output from the analog/digital converter for summing the electrical signals from each detector for each pulse A microprocessor operatively connected to the adding means; and an eventual video output connected to the microprocessor.

It is the primary object of the present invention to provide a method and apparatus for maximizing the delivery of therapeutic radiation to a patient's tumor bearing site while minimizing the amount of radiation delivered to other portions of the patient's body, by providing on-line monitoring of the patient's position within the irradiation portal. This and other objects of the invention will become clear from an inspection of the detailed description of the invention, and from the appended claims.

BRIEF DESCRIPTION OF THE DRAWINGS

FIG. 2 is a schematic top plan view of one form of solid-state detectors utilizable in practicing the present invention;

FIG. 3 is a view like FIG. 2 illustrating another form of solid-state detector deployment according to the present invention;

FIG. 5 is a block diagram of exemplary electronic logic utilized in practicing the present invention; and FIG. 6 is a side view of a vertical stack of solid-state detectors, in parallel, that may be utilized in practicing the invention.

DETAILED DESCRIPTION OF THE DRAWINGS

Figure 1:
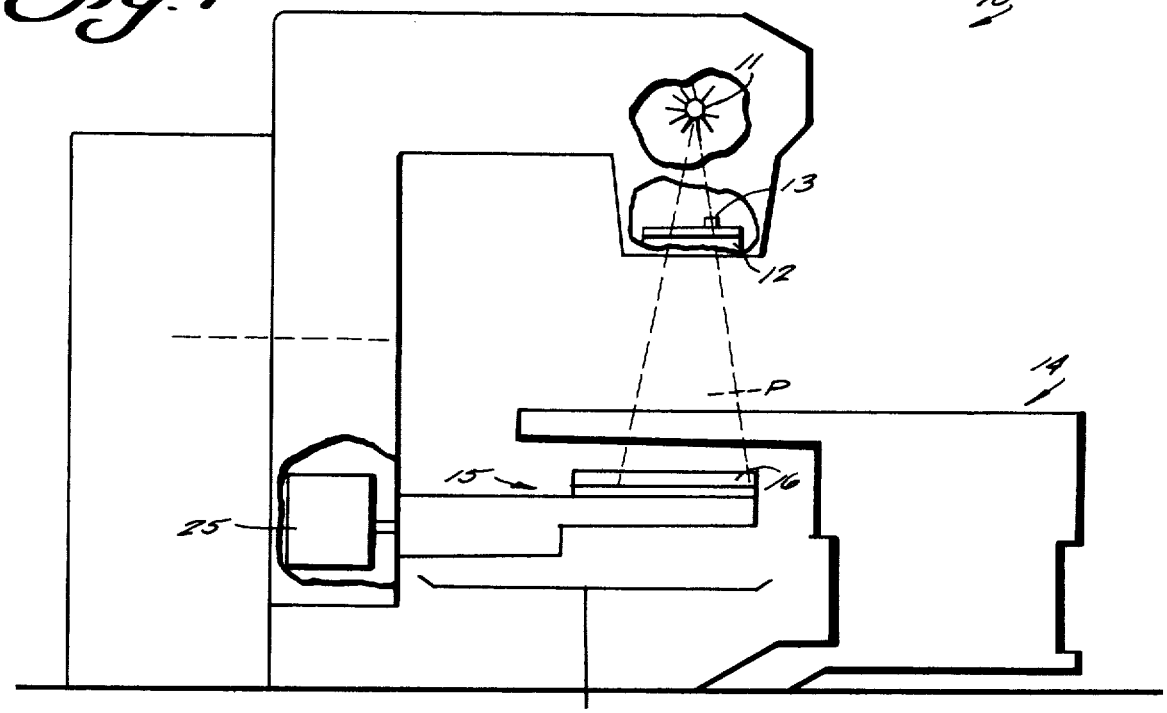
FIG. 1 is a schematic side view illustrating exemplary apparatus according to the present invention.

Apparatus for on-line treatment monitoring for radiation teletherapy according to the present invention is illustrated schematically in the drawings. The apparatus includes a radiation teletherapy machine 10 for emitting high-energy x-ray pulses from a radiation source 11, in an irradiation portal P. A focused block tray 12 and monitoring detectors 13 may be provided in the teletherapy machine, as indicated in FIG. 1. The apparatus further includes a patient treatment couch 14. Located on the opposite side of the patient treatment couch 14 as the teletherapy machine 10 are detecting means (shown schematically at 15 in FIG. 1) for detecting high-energy x-rays emitted from the teletherapy machine 10 and transforming the x-rays to electrical signals. Shielding means (i.e. filtering means), such as a lead plate, are provided covering the detecting means 15 for preventing low energy scattered radiation from reaching the detecting means. Such shielding means are illustrated generally at 16 in FIG. 1. The lead plate 16 may be about the maximum electronic buildup in thickness. This may commonly be within the range of about 0.5–3 mm. The basic apparatus further comprises means for converting the electrical signals produced by the detecting means 15 to a readable display providing patient landmarks of the irradiation portal.

Figure 4:
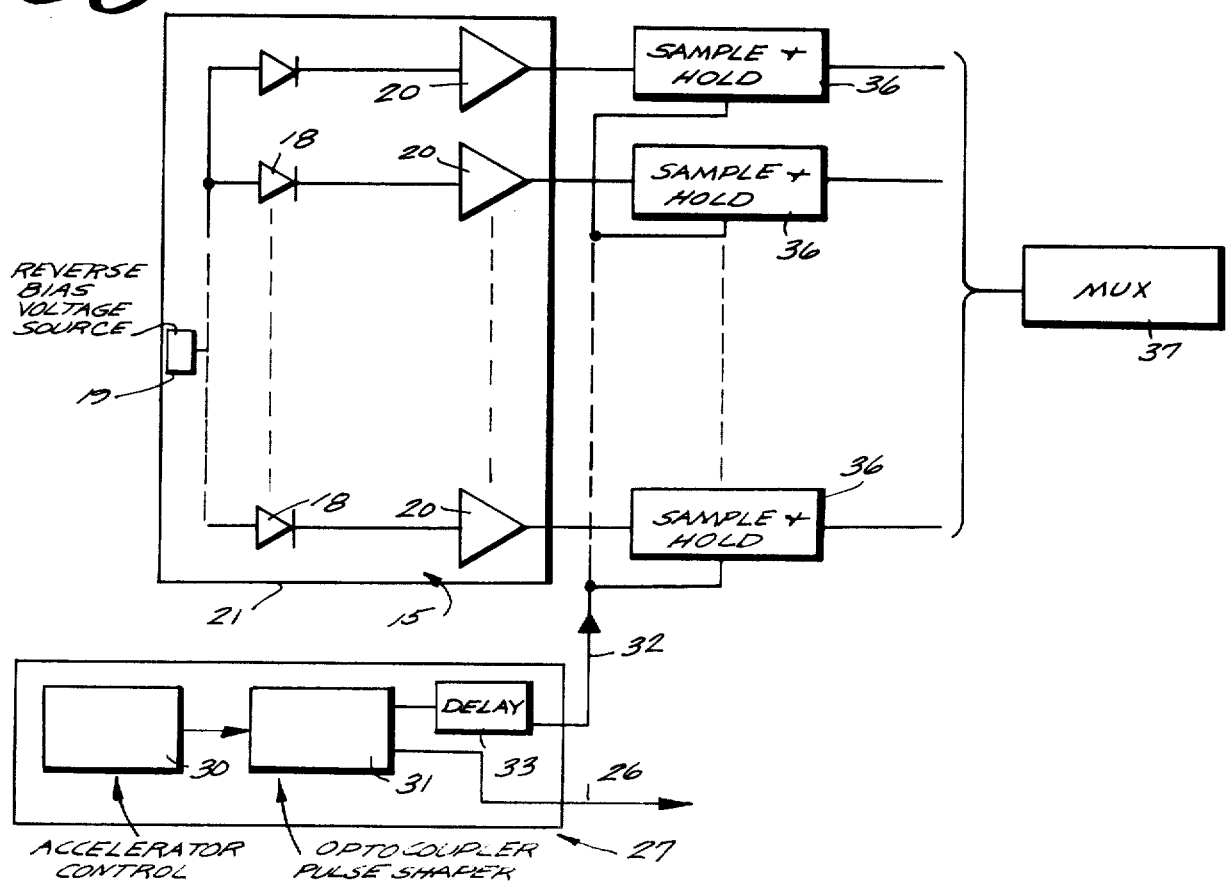
FIG. 4 is a diagrammatic view of a portion of exemplary circuitry means utilized in the apparatus according to the invention.

The detecting means 15 preferably comprise a plurality of solid-state detectors, such as the high voltage rectifier diodes 18 illustrated in the drawings (see FIG. 4 in particular). The solid-state detectors may be made of silicon, mercuric iodide, cadmium telluride, or the like. In general high effiency photon detectors having an Z of about 14 or greater are preferred (Z equals 14 for silicon). A preferred silicon diode detector 18 has a rating of 1,000 volts peak reverse voltage, and 3 amperes average forward DC current. FIG. 4 illustrates the case where the anodes of silicon diode detectors 18 are connected and can either be grounded or connected to a reverse bias voltage source 19. A reverse bias voltage (e.g. 30 volts) tends to increase resolution. The cathodes of the diode detectors 18 illustrated in FIG. 4 are preferably connected to the input of a preamplifier 20, the diode detectors 18 and preamplifiers 20 providing a basic detector array 21. The charge generated at the diode detector by the pulsed x-rays is integrated and amplified by the low noise monolithic preamplifiers 20. However, high gain, high input impedance amplifiers generally may be used. Preferred preamplifiers would have a bipolar transistor input with an output capable of driving a 50 OHM coaxial cable.

The detectors 18 may be disposed in a two-dimensionsal matrix M operatively covering the irradiation portal, as illustrated in FIG. 2. Preferably the detectors may be disposed in at least one linear array L, as illustrated in FIG. 3 (wherein 10 such linear arrays are illustrated). In one operative embodiment according to the invention, the diameter of the silicon chips 18 is 2 mm, and they are mounted on printed circuit boards with separations of 10 mm for a broad scan, or 4 mm for a narrow scan. Diodes 18 may be vertically stacked (see FIG. 6), as in pairs, and disposed in parallel. When stacked, metal plates 23 are disposed between diodes 18, to increase detector efficiency. In the matrix M a single conductor (e.g. a conductor disposed on the bottom surfaces of the detectors 18) connects each row of detectors, while a single conductor (e.g. a single conductor connecting the detectors 18 at the top surfaces thereof) connects the detectors 18 in each column. In the linear arrays L, a single detector also connects each row of detectors.

When using the linear array configuration illustrated in FIG. 3, means for stepping the arrays L over at least a portion of the irradiation portal in sync with the emission of x-ray pulses from the radiation teletherapy machine 10 are provided. Such stepping means preferably comprises a conventional stepping motor, illustrated schematically at 25 in the drawings. As illustrated most clearly in FIG. 5, an output 26 from the accelerator synchronizer 27 of the teletherapy machine 10 is fed to the microprocessor 28, which in turn controls stepping motor 25 through output 29. The array L need only be moved a few millimeters during each step. As illustrated most clearly in FIG. 4, the accelerator synchronizer 27 includes the accelerator control 30, and an optocoupler pulse shaper 31 connected to output 26. Additionally, another output 32 preferably is provided connected to optocoupler pulse shaper 31 through time delay 33, optocoupler pulse shaper 31 isolating the ground of the teletherapy machine 10 from the ground of detectors 18.

For each beam burst, preferably all the detectors 18 in the array must be digitized and normalized to the intensity of the pulse. While a separate digitizer can be provided for each detector channel, it is preferable to hold the signal, utilizing sample and hold amplifiers 36, until an analog/digital converter 38, has time to digitize the signal before switching to the next channel by the multiplexer 37. While a single multiplexer 37 and A/D converter 38 may be utilized for all the sample and hold amplifiers 36, if the number of sample and holds 36 is large more than one multiplexer 37 and A/D converter would be desirable. Output 32 from time delay 33 of the accelerator synchronizer 27 keeps the sample and holds 36 in sync with the teletherapy machine 10 pulses, holding the signals for about one accelerator period, i.e., the interval between pulses until they are passed by the multiplexer to the A/D converter. The sequencing of the multiplexer 37 is also controlled by the microprocessor 28 (as schematically shown in FIG. 5), the microprocessor 28 also reading the digital data into memory.

The system noise can be reduced by increasing the counting statistics. This is accomplished utilizing an adding unit 39 for summing the digital information from the converter 38 from each detector for a plurality of pulses, and feeding the information ultimately to the microprocessor 28 (see FIG. 5). The data from the microprocessor 28 can either be directly video displayed by feeding it to a digital/analog converter 40 and then to a video output 41 and/or it may be put on magnetic tape, or the like, and may be automatically compared to previous displays from the patient when positioning was correct to automatically indicate position changes that need be effected. The tape, etcetera of course may be stored for future reference or analysis.

The preamplifiers 20, sample and holds 36, multiplexer 37, A/D converter, microprocessor 28, adding unit 39, D/A converter 40, and video output 41 comprise a preferred form of the means for converting the electrical signals produced by the detecting means 15 to a readable display providing patient landmarks of the irradiation portal. All detectors are scanned after each pulse, and the resolution of the video output utilizing such a system is far superior to that normally obtained utilizing film.

Utilizing the apparatus illustrated in the drawings, it is possible to practice a method of treating a patient with radiation therapy utilizing a radiation teletherapy machine 10 having high-energy x-rays that provides for on-line monitoring of the patient, maximizing the delivery of therapeutic radiation to the tumor bearing site while minimizing the radiation delivered to other body portions. The exemplary method according to the present invention comprises the following steps:

(a) Positioning the patient in the irradiation portal P of the radiation teletherapy machine 10 in a supposed effective treatment position. (b) While the patient is being irradiated the transmitted radiation detected during the pulses is transformed to electrical signals. This is preferably practiced by providing a plurality of solid-state detectors in a position (see FIG. 1) on the opposite side of the patient as the radiation teletherapy machine 10 radiation source 11, and positioning lead shielding 16 over the solid-state detectors 15. Where a linear array L is used (see FIG. 3) the stepping motor 25 is actuated in sync with the radiation pulses (controlled by synchronizer 27 through line 26) to step the arrays over at least a portion of the irradiation portal P.

The method also includes the following steps: (c) Immediately automatically converting the electrical signals to a readable display providing the landmarks of the irradiation portal. This may be accomplished utilizing the preamplifiers 20, sample and holds 36, multiplexer 37, A/D converter 38, adding unit 39, microprocessor 28, D/A converter 40, and video output 41. (d) Comparing the patient's position as defined by the landmarks to a predetermined desired position for effective treatment. (e) Immediately halting the irradiation if necessary and adjusting the patient's position with respect to the irradiation portal so that it is proper for effective treatment to be continued. The further step (f) may be practiced of repeating steps (b) through (e) until the patient's position corresponds exactly to that desired. The method according to the invention may also consist essentially of the above-described steps performed for every treatment session with no film processing, filming sessions, delays, or the like being necessary (as are inherent conventional procedures).

It will thus be seen that according to the present invention a method and apparatus have been provided for maximizing the amount of prescribed radiation delivered to a tumor site by a radiation teletherapy machine, while minimizing the radiation delivered to other body parts. While the invention has been described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and devices.

What is claimed is:

1. A method of treating a patient with radiation therapy utilizing a radiation teletherapy machine capable of emitting high-energy x-rays, comprising the steps of:

(a) positioning the patient in the irradiation portal of the radiation teletherapy machine in a supposed effective treatment position;

(b) effecting operation of the machine to emit a therapy beam, and only a therapy beam, of high-energy pulses for effective patient treatment;

(c) automatically detecting only the high-energy pulses and transforming the radiation detected during the pulses to electrical signals, by providing at least one linear array of solid-state detectors in a position on the opposte side of the patient as the fixed beam radiation teletherapy machine, and stepping the at least one linear array over at least a portion of the irradiation portal in sync with the pulses from the radiation teletherapy machine;

(d) immediately converting the electrical signals to a readable display providing the landmarks of the irradiation portal;

(e) comparing the patient's position as defined by the landmarks to a predetermined desired position for effective treatment;

(f) immediately halting irradiation if the portal is outside the acceptable margin;

(g) adjusting the patient's position with respect to the irradiation portal so that it is proper for effective treatment; and (h) continuing radiation therapy to deliver the desired dosage of radiation to the patient.

2. A method as recited in claim 1 wherein step (c) is further practiced by positioning filtering means over the detectors to prevent low energy scattered radiation from reaching the detectors.

3. A method as recited in claim 1 comprising the further step (i) of, repeating steps (b) through (g) until the patient's position corresponds exactly to that desired.

4. The method of claim 1 wherein the readable display of step (d) is recorded.

5. A method as recited in claim 1 wherein step (d) is practiced by automatically processing and digitizing the electrical signals in synchronization with the radiation teletherapy machine pulses, and summing the electrical signals from each detector.

6. A method as recited in claim 5 wherein step (d) is further practiced by automatically converting the summed signals to analog information, and converting the analog information to a video display.

7. A method as recited in claim 5 wherein step (d) comprises the further step of feeding the summed digitized information to a microprocessor.

8. A method as recited in claim 1 wherein step (d) is practiced by amplifying the electrical signals, and sampling and holding the signals in sync with the radiation teletherapy machine pulses.

9. A method as recited in claim 8 wherein step (d) is further practiced by reading the signals from the sample and holds with a multiplexer, converting the signals to digital information, summing the digital information from each detector for a plurality of pulses, feeding the information to a microprocessor, and feeding the information from the microprocessor to an ultimate display station.

10. A method as recited in claim 8 comprising the further step of isolating grounds for the solid-state detectors and the radiation teletherapy machine utilizing an opto-coupler.

11. A method as recited in claim 1 wherein step (d) is practiced in part by scanning all detectors after each pulse.

12. A method as recited in claims 1 or 2 consisting essentially of said steps.

13. Apparatus for on-line treatment monitoring for radiation teletherapy, comprising
a radiation teletherapy machine for emitting high-energy x-ray pulses in a therapy beam, and only a therapy beam, in an irradiation portal;
a patient treatment couch;
detecting means for detecting only the high-energy x-rays emitted from said radiation teletherapy machine and transforming the x-rays detected to electrical signals, said means located on the opposite side of said patient treatment couch as said radiation teletherapy machine, said detecting means comprising a plurality of solid-state detectors disposed in a two-dimensional matrix operatively covering the irradiation portal;
filtering means covering said detecting means for preventing low energy scattered radiation from reaching said detecting means; and
means for converting the electrical signals produced by said detecting means to a readable display providing patient landmarks of the irradiation portal.

14. Apparatus as recited in claim 13 wherein said solid-state detectors are composed of materials selected from the group consisting essentially of silicon, cadmium telluride, and mercuric iodide.

15. Apparatus as recited in claim 13 wherein said solid-state detectors are detectors operable at room temperature having an effective atomic number Z greater than or equal to about 14.

16. Apparatus as recited in claim 13 wherein said means for converting the electrical signals produced by said detecting means to a readable display comprise an amplifier associated with each detector; a sample and hold means associated with each detector; and means for connecting said sample and hold means to said radiation teletherapy machine through a pulse shaping and time delay for controlling said sample and hold means.

17. Apparatus as recited in claim 16 further comprising an opto-coupler for isolating the ground of said radation teletherapy machine from the ground of said detectors.

18. Apparatus as recited in claim 16 wherein said means for converting the electrical signals produced by said detecting means to a readable display further comprise analog/digital converter means operatively attached to the output from said sample and hold means; adding means operatively attached to the output from said analog/digital converter means for summing the electrical signals from each detector; and a microprocessor operatively connected to said adding means.

19. Apparatus as recited in claim 16 wherein said means for converting the electrical signals produced by said detecting means to a readable display further comprise a multiplexer connected to the output from said sample and hold means, and an analog/digital converter operatively connected to said multiplexer.

20. Apparatus as recited in claims 13, or 16 consisting of the recited components.

21. Apparatus as recited in claim 13 wherein said detectors are arranged in at least one horizontal line, and in parallel in vertical stacks, a metal sheet being provided between the detectors in each vertical stack to thereby increase detection efficiency.

22. Apparatus as recited in claim 13 wherein a single conductor is connected to each row of detectors, and a single conductor to each column of detectors, in said matrix.

23. Apparatus as recited in claim 13 wherein said solid-state detectors comprise silicon diodes.

24. Apparatus as recited in claim 23 wherein the anodes of said diodes are connected to a reverse bias voltage source.

25. Apparatus as recited in claim 23 wherein said diodes are horizontally spaced from each other in a grouping disposed in the irradiation portal.

* * * * *